(12) United States Patent
Pergolizzi et al.

(10) Patent No.: US 9,962,371 B2
(45) Date of Patent: May 8, 2018

(54) READY TO USE KETOROLAC FORMULATIONS

(71) Applicant: RTU PHARMACEUTICALS, LLC, Naples, FL (US)

(72) Inventors: Joseph V. Pergolizzi, Naples, FL (US); Alexander Mironov, Naples, FL (US); Chad James Pickens, Bend, OR (US); Douglas Giles Johnson, Arvada, CO (US)

(73) Assignee: RTU PHARMACEUTICALS, LLC, Naples, FL (US)

( * ) Notice: Subject to any disclaimer, the term of this patent is extended or adjusted under 35 U.S.C. 154(b) by 0 days. days.

(21) Appl. No.: 15/211,560

(22) Filed: Jul. 15, 2016

(65) Prior Publication Data
US 2017/0007575 A1    Jan. 12, 2017

Related U.S. Application Data

(63) Continuation of application No. 13/278,703, filed on Oct. 21, 2011, now Pat. No. 9,421,191.

(60) Provisional application No. 61/481,602, filed on May 2, 2011, provisional application No. 61/405,384, filed on Oct. 21, 2010.

(51) Int. Cl.
| | | |
|---|---|---|
| *A61K 31/407* | (2006.01) | |
| *A61K 9/00* | (2006.01) | |
| *A61K 47/26* | (2006.01) | |
| *A61K 9/08* | (2006.01) | |

(52) U.S. Cl.
CPC .......... *A61K 31/407* (2013.01); *A61K 9/0019* (2013.01); *A61K 9/08* (2013.01); *A61K 47/26* (2013.01)

(58) Field of Classification Search
CPC .................................................. A61K 31/407
See application file for complete search history.

(56) References Cited

U.S. PATENT DOCUMENTS

| | | | |
|---|---|---|---|
| 4,089,969 | A | 5/1978 | Muchowski |
| 6,509,027 | B2 | 1/2003 | Sands et al. |
| 7,635,773 | B2 | 12/2009 | Antle |
| 2003/0191187 | A1 | 10/2003 | Lee et al. |
| 2006/0188530 | A1 | 8/2006 | Yoo |
| 2007/0049552 | A1 | 3/2007 | Babu et al. |
| 2007/0142478 | A1 | 6/2007 | Xia et al. |
| 2007/0203173 | A1 | 8/2007 | Mudumba et al. |
| 2008/0057023 | A1 | 3/2008 | Chynn et al. |
| 2008/0262017 | A1 | 10/2008 | Ulloa et al. |
| 2008/0312154 | A1 | 12/2008 | Peterlin |
| 2008/0317681 | A1 | 12/2008 | Gebreselassie et al. |
| 2009/0060989 | A1 | 3/2009 | Cevc et al. |
| 2009/0227534 | A1 | 9/2009 | Garcia-Salgado Lopez et al. |
| 2009/0239836 | A1 | 9/2009 | Ciolkowski et al. |
| 2009/0263319 | A1 | 10/2009 | Wohabrebbi et al. |
| 2010/0011046 | A1 | 1/2010 | Moon et al. |
| 2010/0166756 | A1 | 7/2010 | Cohen et al. |
| 2015/0157560 | A1* | 6/2015 | Jacobson ............... A61K 31/64 514/593 |

FOREIGN PATENT DOCUMENTS

WO    2009087658    7/2009

OTHER PUBLICATIONS

European Search Report for PCT/US2011057284 dated Jun. 20, 2016.
Gupta V D et al: "Stability of ketorolac tromethamine in 5% dextrose injection and 0.9% sodium chloride injections", International Journal of Pharmaceutical Compounding, vol. 1, No. 3, May 1, 1997, pp. 206-207.
Andy Shi, et al., "Stability of Ketorolac Tromethamine in IV Solutions and Waste Reduction", CJHP vol. 53, No. 4, Oct. 2000, pp. 263-269.
Kowaluk et al. American Journal of Health System pharmacy, 1981, vol. 38, No. 9, Abstract.
International Search Report for PCT/US2011/057284 dated Feb. 27, 2012, 3 pgs.
Written Opinion of the International Searching Authority for PCT/US2011/057284 dated Feb. 27, 2012, 11 pgs.
International Preliminary Report on Patentability for PCT/US2011/057284 dated Apr. 23, 2013, 12 pgs.
Floy, Barbara J., et al., "Compatibility of Ketorolac tTomethamine injection with common infusion fluids and administration sets," American Journal of Hospital Pharmacy, May 1990, vol. 47, 1097-1100.
SPRIX Highlights of Prescribing Information, Apr. 2014, 30 pgs.
ACUVAIL Highlights of Prescribing Information, Nov. 2012, 6 pgs.

* cited by examiner

*Primary Examiner* — Samira Jean-Louis
(74) *Attorney, Agent, or Firm* — Lowenstein Sandler LLP

(57) ABSTRACT

Disclosed in certain embodiments is a pharmaceutical composition for parenteral administration comprising:
an aqueous solution comprising ketorolac or a pharmaceutically acceptable salt thereof in an amount from about 0.1 mg/mL to about 10 mg/mL; and
a pharmaceutically acceptable excipient;
wherein the formulation is substantially free of alcohol.

21 Claims, 1 Drawing Sheet

*Long-term Predicted Stability of Formulations 7, 8, and 10 at 25°C*
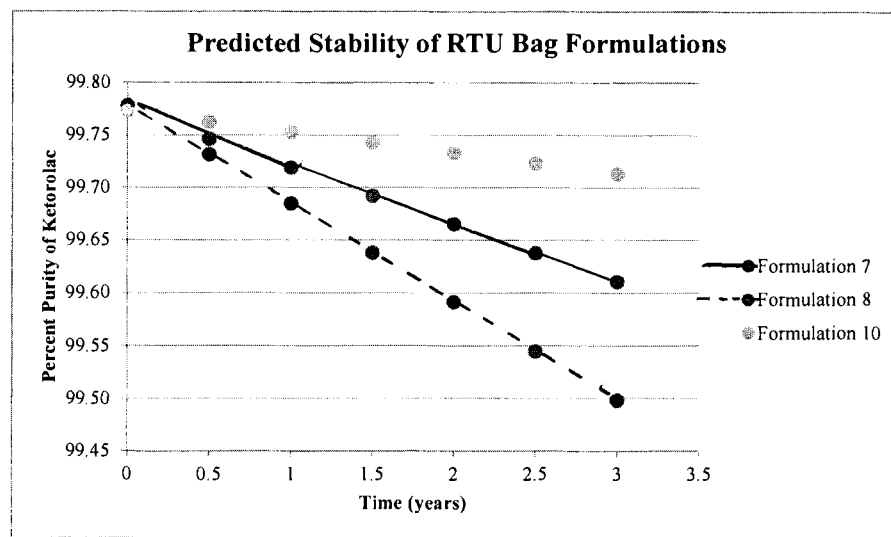

READY TO USE KETOROLAC FORMULATIONS

BACKGROUND

This application claims priority to U.S. Provisional Application No. 61/405,384 filed Oct. 21, 2010, and U.S. Provisional Application No. 61/481,602 filed May 2, 2011, the disclosure of which are both hereby incorporated by reference in their entireties.

Ketorolac or 5-benzoyl-2,3-dihydro-1H-pyrrolizine-1-carboxylic acid, is a known non-steroidal anti-inflammatory agent and has analgesic and anti-inflammatory properties. Ketorolac is described in U.S. Pat. No. 4,089,969.

Ketorolac has considerably higher analgesic and anti-inflammatory activity than many other non-steroid anti-inflammatory drugs. Most significantly, it has higher analgesic activity than morphine, without the well-known side effects of the latter. See, e.g., "Ketorolac—A review of its pharmacodynamic and pharmacokinetic properties and its therapeutic potential", Drugs 39(1): 86-109, 1990.

The drug is currently administered as the racemic mixture orally or by injection and is commercially available in forms suited for such modes of delivery. Ketorolac tromethamine salt for intramuscular and intravenous administration is available at concentrations ranging from 1.5% (15 mg in 1 ml) to 3% (60 mg in 2 mls). Typically, for multi-dose treatment, the recommended dose is 30 mg of drug every 6 hours. In certain situations, the drug is given as a loading dose of 30 to 60 mg followed by subsequent injections of half the loading dose (15 to 30 mg) every 6 to 8 hours. The total daily dose of the drug as such is in the range of 60-120 mg. The administration of multiple injections is not convenient or well tolerated by patients and bolus administration of the drug either intravenously or intramuscularly can result in a higher incidence of side effects.

Ketorolac is also available as oral tablets and nasal spray. However, these formulations are insufficient to manage moderately severe acute pain that requires analgesia at the opioid level, e.g., in a post operative setting.

Although continuous infusion of ketorolac has been contemplated, the preparation of such formulations in an acute setting has issues with respect to dosing errors, safety issues and maintaining a sterile, stable formulation.

There exists a need in the art for a ready to use ketorolac formulation that is suitable for direct administration to patients for the treatment of analgesia, e.g., in an acute post-operative setting.

All references disclosed herein are hereby incorporated by reference in their entireties for all purposes.

OBJECTS AND SUMMARY OF THE INVENTION

It is an object of the present invention to provide a pharmaceutical composition for parenteral administration comprising: ketorolac or a pharmaceutically acceptable salt thereof and a pharmaceutically acceptable excipient; wherein the composition requires no dilution prior to administration.

It is an object of the present invention to provide a method of treating a ketorolac treatable condition comprising administering to a patient having a ketorolac treatable condition a composition, a parenteral formulation comprising: ketorolac or a pharmaceutically acceptable salt thereof and a pharmaceutically acceptable excipient; wherein the composition requires no dilution prior to administration.

It is an object of the present invention to provide a method of reducing dosage administration errors in administering ketorolac comprising providing a pharmaceutical composition for parenteral administration comprising: ketorolac or a pharmaceutically acceptable salt thereof and a pharmaceutically acceptable excipient; wherein the composition requires no dilution prior to administration.

It is an object of the present invention to provide a method of reducing pharmaceutical active substance wastage in formulation of ketorolac introduced by use of partial vial usage, which method comprises providing a pharmaceutical composition for parenteral administration comprising: ketorolac or a pharmaceutically acceptable salt thereof and a pharmaceutically acceptable excipient; wherein the composition requires no dilution prior to administration.

It is an object of the present invention to provide a method of preparing a pharmaceutical composition comprising combining ketorolac or a pharmaceutically acceptable salt thereof with an excipient to produce a pharmaceutical composition for parenteral administration wherein the composition requires no dilution prior to administration.

It is an object of the present invention to provide a method of providing analgesia while reducing the amount of opioids (i.e., opioid sparing) administered to a patient, the method comprising administering a ready to use ketorolac parenteral formulation by continuous infusion to a patient in need thereof.

It is an object of the present invention to provide a method of providing analgesia while reducing the amount of NSAIDs (i.e., NSAID sparing) administered to a patient, the method comprising administering a ready to use ketorolac parenteral formulation by continuous infusion to a patient in need thereof.

The opioid sparing and NSAID sparing formulations may have benefits that include decreased respiratory depression, decreased nausea and vomiting and/or decreased length of hospital stay.

It is an object of the present invention to provide a method of providing analgesia comprising administering a bolus dose of ketorolac to achieve a rapid analgesic response, followed by continuous infusion with a ready to use ketorolac parenteral formulation to maintain analgesic response. In the methods disclosed herein, bolus dosing can be, e.g., from about 10 mg to about 50 mg, from about 20 mg to about 40 mg, or about 30 mg and continuous infusion can be, e.g., from about 0.5 mg to about 5 mg per hour, from about 1 mg to about 4 mg per hour, or from about 2 mg to about 3 mg per hour.

It is an object of the present invention to provide a method of reducing the peak to trough plasma levels of multiple bolus administration of ketorolac comprising administering by continuous infusion, a ready to use ketorolac parenteral formulation to provide analgesia.

It is an object of the present invention to provide a method of reducing postop illeus comprising administering a ready to use ketorolac parenteral formulation by continuous infusion to a patient in need thereof.

It is an object of the present invention to provide a method of treating analgesia (e.g., obtaining minimum effective analgesic concentration "MEAC") comprising administering by continuous infusion a ready to use ketorolac formulation as disclosed herein.

It is an object of the present invention to provide a method of reducing the daily dose of ketorolac necessary to obtain analgesia comprising administering by continuous infusion, a ready to use ketorolac parenteral formulation. In certain embodiments, effective analgesia is obtained with a daily dose from about 50 mg to about 110 mg, from about 60 mg to about 80 mg, or from about 78 mg to about 102 mg.

It is an object of the present invention to provide a method of reducing the peak to trough plasma levels of multiple bolus administration of ketorolac comprising administering by continuous infusion, a ready to use ketorolac parenteral formulation to provide analgesia.

It is an object of the present invention to provide a method of reducing side effects associated with ketorolac comprising administering by continuous infusion, a ready to use ketorolac parenteral formulation to provide analgesia.

The above objects of the invention and others may by the present invention which in certain embodiments is directed to a pharmaceutical composition for parenteral administration comprising an aqueous solution comprising ketorolac or a pharmaceutically acceptable salt thereof in an amount from about 0.1 mg/mL to about 10 mg/mL; and a pharmaceutically acceptable excipient; wherein the formulation is substantially free of alcohol.

In certain embodiments, the invention is directed to a pharmaceutical composition for parenteral administration comprising an aqueous solution comprising ketorolac or a pharmaceutically acceptable salt thereof in an amount from about 0.1 mg/mL to about 1 mg/mL; and from about 0.1% to about 3% dextrose; wherein the composition is contained in a flexible intravenous bag; wherein the formulation has a pH from about 6.0 to about 7.5; and wherein the formulation maintains at least 90% of the amount of ketorolac or a pharmaceutically acceptable salt thereof after storage for 6 months.

In certain embodiments, the present invention is directed to a pharmaceutical composition for parenteral administration comprising an aqueous solution comprising ketorolac or a pharmaceutically acceptable salt thereof in an amount from about 0.1 mg/mL to about 1 mg/mL; and trehalose; wherein the composition is contained in a flexible intravenous bag; wherein the formulation has a pH from about 6.0 to about 7.5; and wherein the formulation maintains at least 90% of the amount of ketorolac or a pharmaceutically acceptable salt thereof after storage for 6 months.

In certain embodiments, the present invention is directed to a pharmaceutical composition for parenteral administration comprising an aqueous solution comprising ketorolac or a pharmaceutically acceptable salt thereof in an amount from about 0.1 mg/mL to about 1 mg/mL; and from about 0.1% to about 10% trehalose; wherein the composition is contained in a flexible intravenous bag; wherein the formulation has a pH from about 6.5 to about 7.3; and wherein the formulation maintains at least 90% of the amount of ketorolac or a pharmaceutically acceptable salt thereof after storage for 6 months.

In certain embodiments, the present invention is directed to a pharmaceutical composition for parenteral administration comprising an aqueous solution comprising ketorolac or a pharmaceutically acceptable salt thereof in an amount from about 0.1 mg/mL to about 1 mg/mL; and a pharmaceutically acceptable excipient; wherein the composition has an activation energy ($E_a$) of at least 60 kJ/mol; and wherein the formulation maintains at least 90% of the amount of ketorolac or a pharmaceutically acceptable salt thereof after storage for 6 months.

The term "ketorolac" means ketorolac free acid or any pharmaceutically acceptable salt thereof, e.g., ketorolac tromethamine. The term also is meant to encompass the racemate as well as the dextro and levo isomers.

The term "ready to use" means a formulation that does not need to be compounded at the time of administration or at a time just prior (e.g., 1 hour, 12 hours, 24 hours, 1 day, 3 days or 7 days) to administration of the formulation.

The concentrations of ketorolac disclosed herein can be calculated based on the salt form as an equivalent amount of the free acid form.

BRIEF DESCRIPTION OF THE DRAWINGS

FIG. 1 depicts the one and two year purity projections for formulations 7, 8 and 10.

DETAILED DESCRIPTION

The present invention is directed to a pharmaceutical composition for parenteral administration comprising: ketorolac or a pharmaceutically acceptable salt thereof and a pharmaceutically acceptable excipient in a ready to use formulation, i.e., wherein the composition is requires no dilution prior to administration is suitable for administration at the point of manufacture, without the need for hospital personnel to dilute and/or prepare parenteral formulations contemporaneous with use. The excipients utilized in the present invention can include, e.g., a solubilizing agent, antioxidant (e.g., vitamin E, vitamin C or glutathione), buffering agent, acidifying agent, complexation enhancing agent, saline, dextrose, lyophilizing aid, bulking agent, stabilizing agents, electrolyte, another therapeutic agent, alkalizing agent, antimicrobial agent, antifungal agent or a combination thereof.

The present invention meets the unmet need of a ready to use storage stable ketorolac formulation wherein it is not necessary for hospital personnel to rely upon admixed formulations that are prepared from a commercially available concentrated product. Admixing a concentrated product has the potential to lead to undesired consequences such as an unsterile product, an unstable product, dosing errors, safety issues for staff.

In certain embodiments, the present invention provides a storage stable pharmaceutical formulation of ketorolac in unconcentrated form. These formulations are stable for extended periods even with the increased solvent:drug ratio and container surface:drug ratio as compared to concentrated formulations, which would be expected to lead to increased degradation of the drug. Further, the commercially available concentrated product contains ethanol which is generally not desirable to be administered to a patient or included in flexible plastic containers for an extended period.

In certain embodiments, the formulations of the present invention maintain at least 90% of the amount of ketorolac or a pharmaceutically acceptable salt thereof after storage for 6 months; maintain at least 90% of the amount of ketorolac or a pharmaceutically acceptable salt thereof after storage for 1 year; or maintain at least 90% of the amount of ketorolac or a pharmaceutically acceptable salt thereof after storage for 2 years.

In certain embodiments, the formulations of the present invention maintain at least 95% of the amount of ketorolac or a pharmaceutically acceptable salt thereof after storage for 6 months; maintain at least 95% of the amount of ketorolac or a pharmaceutically acceptable salt thereof after storage for 1 year; or maintain at least 95% of the amount of ketorolac or a pharmaceutically acceptable salt thereof after storage for 2 years.

In certain embodiments, the formulations of the present invention maintain at least 98% of the amount of ketorolac or a pharmaceutically acceptable salt thereof after storage for 6 months; maintain at least 98% of the amount of ketorolac or a pharmaceutically acceptable salt thereof after storage for 1 year; or maintain at least 98% of the amount of ketorolac or a pharmaceutically acceptable salt thereof after storage for 2 years.

In certain embodiments, the ketorolac or a pharmaceutically acceptable salt thereof is present in the formulation in an amount from about 0.01 mg/mL to about 10 mg/mL, from about 0.1 mg/mL to about 5 mg/mL, from about 0.25 mg/mL to about 1 mg/mL, or about 0.3 mg/mL, or about 0.4 mg/mL, or about 0.5 mg/mL, or about 0.6 mg/mL, or about 0.7 mg/mL, or about 0.8 mg/mL, or about 0.9 mg/mL.

In certain embodiments, the pH of the ready to use solution has is from about 2.5 to about 8.5, from about 3.5 to about 7.5, from about 3.5 to about 5.5, from about 3.5 to about 4.5, from about 4.5 to about 8.5, from about 4.5 to about 7.5, from about 6.8 to about 7.6, or from about 6.9 to about 7.5.

The pH of the compositions of the present invention can be modified by utilizing a sufficient amount of a pH adjuster selected from the group consisting of an acid and a base. Suitable pH adjusters typically include at least an acid or a salt thereof, and/or a base or a salt thereof. Acids and bases can be added on an as needed basis in order to achieve a desired pH. For example, if the pH is greater than the desired pH, an acid can be used to lower the pH to the desired pH. Acids suitable for use in premixed pharmaceutical compositions include, but are not limited to, hydrochloric acid, phosphoric acid, citric acid, ascorbic acid, acetic acid, sulphuric acid, carbonic acid and nitric acid. In some embodiments, hydrochloric acid is used to adjust the pH. By way of another example, if the pH is less than the desired pH, a base can be used to adjust the pH to the desired pH. Bases suitable for use in premixed pharmaceutical compositions include, but are not limited to, sodium hydroxide, potassium hydroxide, calcium hydroxide, sodium carbonate, sodium citrate, sodium acetate, and magnesium hydroxide.

The parenteral compositions described herein can also utilize a pharmaceutically acceptable buffer. Suitable buffers include, but are not limited to, pharmaceutically acceptable salts and acids of acetate, glutamate, citrate, tartrate, benzoate, lactate, histidine or other amino acids, gluconate, phosphate, malate, succinate, formate, propionate, and carbonate. In certain embodiments, the buffer can be included in the composition of the present invention in a amount from about 0.0001 mg/mL to about 100 mg/mL, from about 0.0001 to about 0.001 mg/mL, from about 0.001 to about 0.01 mg/mL, from about 0.01 to about 0.1 mg/mL, from about 0.1 to 1 mg/mL, from about 1 to about 5 mg/mL, from about 5 to about 10 mg/mL, from about 10 to about 15 mg/mL, from about 15 to about 20 mg/mL, from about 20 to about 25 mg/mL, from about 25 to about 50 mg/mL, from about 50 to about 75 mg/mL, or from about 75 to about 100 mg/mL.

In other embodiments, the buffer is at least one member selected from the group consisting of at least one of (1) a carboxylic acid, a hydroxy carboxylic acid, a dicarboxylic acid, with at least of its acid group pKa(s) greater than 3.0, a salt thereof, or a mixture of said carboxylic acid and said salt thereof and (2) an alkali metal or ammonium carbonate, alkali metal or ammonium bicarbonate, or mixtures thereof.

In alternative embodiments, the can be, e.g., an acetate buffer, an amino acid buffer, a lactobionic acid buffer, or a carbonate buffer.

Amino acids that can be utilized in the present invention include, e.g., arginine, glycine, methionine or lysine. In certain embodiments, the amino acid has at least one basic group with a pKa of over 5, over 6, over 7 over 8 or over 8.5, or mixtures thereof or a salt thereof, or a mixture of an amino acid and said salt. The amino acid can be present in an amount, e.g., from about 0.1 mg/mL to about 100 mg/mL, from about 1 mg/mL to about 50 mg/mL or from about 5 mg/mL to about 25 mg/mL.

Carboxylic acids that can be utilized in the present invention include, e.g., gluconic acid, glucuronic acid, gluconic acid ethers, glucuronic acid ethers, carbonic acid alkali metal salts, carbonic acid ammonium salts and mixtures thereof.

The parenteral compositions of the present invention can be hypotonic, isotonic or hypertonic. Preferably, the parenteral formulations have a tonicity from about 250 to about 350 mOsm/kg.

Any pharmaceutically acceptable tonicity agent can be utilized in the formulations of the present invention. Suitable tonicity agents include, but are not limited to, anhydrous or hydrous forms of sodium chloride, dextrose, sucrose, xylitol, fructose, glycerol, sorbitol, mannitol, potassium chloride, mannose, calcium chloride, magnesium chloride and other inorganic salts. Preferably, the tonicity agent is dextrose or sodium chloride.

The tonicity agent can be utilized in the formulations of the present invention in an amount, e.g., from about 0.1 mg/mL to about 100 mg/mL, from about 1 mg/mL to about 50 mg/mL, from about 50 mg/mL to about 10 mg/mL, from about 30 mg/mL to about 70 mg/mL, from about 1 mg/mL to about 10 mg/mL, from about 5 mg/mL to about 15 mg/mL, from about 65 mg/mL to about 75 mg/mL, or from about 70 mg/mL to about 80 mg/mL.

In embodiments, with dextrose, the amount can be, e.g., from about 0.1% to about 10%, from about 0.2% to about 5%, from about 0.3% to about 3%, or from about 0.5% to about 1.5%.

In order to obtain the ready to use formulation of the present invention, a cosolvent for the ketorolac can be utilized. The cosolvent can include a glycol (e.g., polyethylene glycol, propylene glycol), ethanol, or a polyhydric alcohol (e.g., sorbitol, mannitol, xylitol). The cosolvent can be utilized in the present invention, e.g., in an amount from about 0.1 mg/mL to about 150 mg/mL, in an amount from about 1 mg/mL to about 75 mg/mL, from about 50 mg/mL to about 100 mg/mL, from about 30 mg/mL to about 90 mg/mL, from about 1 mg/mL to about 10 mg/mL, from about 5 mg/mL to about 15 mg/mL, from about 75 mg/mL to about 100 mg/mL, or from about 85 mg/mL to about 125 mg/mL.

Preferably, the formulations of the present invention do not contain ethanol. In embodiments that include ethanol have a preferable concentration of less than 10% v/v, less than 7.5% v/v, less than 5% v/v, less than 2% v/v, less than 1% v/v or less than 0.5% v/v.

In certain embodiments of the present invention, the pharmaceutically acceptable excipient comprises trehalose in an amount, e.g., from about 0.1 mg/mL to about 100 mg/mL, from about 1 mg/mL to about 50 mg/mL, from about 50 mg/mL to about 10 mg/mL, from about 30 mg/mL to about 70 mg/mL, from about 1 mg/mL to about 10 mg/mL, from about 5 mg/mL to about 15 mg/mL, from about 65 mg/mL to about 75 mg/mL, or from about 70 mg/mL to about 80 mg/mL. In certain embodiments, the trehalose is in an amount, e.g., from about 0.1% to about 10%, from about 0.2% to about 5%, from about 0.3% to about 3%, or from about 0.5% to about 1.5%.

The parenteral formulations of the present invention can also include a surfactant, e.g., a non-ionic surfactant. The surfactant can be in an amount, e.g., from about 0.1 mg/mL to about 20 mg/mL, about 0.2 mg/mL to about 10 mg/mL or from about 1 mg/mL to about 5 mg/mL.

Suitable non-ionic surfactants include but are not limited to ethoxylated polysorbate such as polysorbate 80, an ethylene oxide/propylene oxide copolymer, a polyethoxylated castor oil, or a polyethylene glycol hydroxystearate.

The parenteral formulations of the present invention can include a cyclodextrin in order to enhance the solubilization of the ketorolac or pharmaceutically acceptable salt thereof. The active agent can form an inclusion complex with the cyclodextrin, which can be e.g., an alpha, beta or gamma cyclodextrin.

The molar ratio of ketorolac or salt thereof can be, e.g., from about 1:10 to about 10:1, from about 1:5 to about 5:1 or from about 1:3 to about 3:1.

In certain embodiments, the cyclodextrin is a sulfalkylated beta cyclodextrin such as sulfobutylated cyclodextrin or sulfobutylether-beta-cyclodextrin. The average degree of substitution of the cyclodextrin can be, e.g., from about 2 to about 10 degrees of sulfobutylation or from about 5 to about 8 degrees of sulfobutylation. In other embodiments, the cyclodextrin is hydroxypropyl beta cyclodextrin.

In preferred embodiments, the cyclodextrins of the present invention are substantially pure. In particular embodiments, the cyclodextrin has at least one of the following: (i) less than 100 ppm of a phosphate, (ii) less than 20 ppm of a sulfoalkylating agent, (iii) less than 0.5% wt. of an underivatized cyclodextrin, (iv) less than 1% wt. of an alkali metal halide salt or (v) less than 0.25% wt. of a hydrolyzed sulfoalkylating agent.

In particular embodiments, the cyclodextrin has less than 50 ppm of a phosphate; less than 10 ppm of a sulfoalkylating agent; less than 0.2% wt. of an underivatized cyclodextrin; less than 0.5% wt. of an alkali metal halide salt; and less than 0.1% wt. of a hydrolyzed sulfoalkylating agent.

In other embodiments, the cyclodextrin has less than 10 ppm of a phosphate; less than 2 ppm of a sulfoalkylating agent; less than 0.1% wt. of an underivatized cyclodextrin; less than 0.2% wt. of an alkali metal halide salt; and less than 0.08% wt. of a hydrolyzed sulfoalkylating agent.

In further embodiments, the cyclodextrin has less than 5 ppm of a phosphate; less than 0.1% wt. of an alkali metal halide salt; and less than 0.05% wt. of a hydrolyzed sulfoalkylating agent.

In certain embodiments, the osmolality of the formulations are e.g., from about 250 to 350 mOsm/kg, from about 270 to 330 mOsm/kg or from about 290 to 310 mOsm/kg.

In certain embodiments, the pharmaceutical compositions of the present invention have an activation energy ($E_a$) of at least 60 kJ/mol, at least 70 kJ/mol, at least 80 kJ/mol, at least 90 kJ/mol, at least 100 kJ/mol, or at least 110 kJ/mol.

In certain embodiments, the pharmaceutical compositions are sterilized, e.g., by terminal sterilization.

In certain embodiments, the pharmaceutical composition of the present invention has a dissolved oxygen content of less than about 15 mg/L, less than about 12 mg/L or less than about 9 mg/L.

The parenteral compositions of the present invention can be contained in a pharmaceutically acceptable container selected from the group consisting of intravenous bags and bottles. The bags and bottles can be glass or a suitable plastic or polymer material. The entire or substantially the entire container can be, e.g., selected from the group consisting of polyvinyl chloride, polyolefin, polyester, polypropylene or a combination thereof. In other embodiments, only the surface material that contacts the drug formulation comprises these materials. Non-limiting examples of intravenous bags include, but are not limited to: Galaxy®, Intravia®, Solomix®, Stedim 71®, Stedim 1000, Viaflex®, Excel®, Visiv®, Viaflo®, Addease®, Addvantage®, Duplex®, First Choice®, Propyflex®, B. Braun® and BFS®. Other embodiments can use containers manufactured by Pisa® or containers utilizing materials manufactured by Technoflex®.

The bags can have mono or multi (e.g., dual) ports. The bags may also be bifurcated with one section of the bag used for a bolus and the other used for continuous infusion. Bifurcated bags can also be used to house ketorolac and another active agent separately.

The formulations disclosed herein can have an overcoat or pouch (e.g., foil or paper) to protect the active substance from light. In other embodiments, the composition is protected from oxygen by maintaining a nitrogen atmosphere in the space between the formulation container and the overcoat or pouch. In other embodiments, the container (e.g., glass or plastic) can include be manufactured to be light resistant (e.g., an amber bottle or amber bag).

The parenteral ketorolac formulations of the present invention can also include an amount of an opioid analgesic. The opioid analgesic, along with the ketorolac, is in a ready-to use form and can be administered to a patient in need thereof without the need to dilute the product.

The opioid analgesic can be selected from the group consisting of, e.g., alfentanil, allylprodine, alphaprodine, anileridine, apomorphine, apocodeine, ben-zylmorphine, bezitramide, brifentanil, buprenorphine, butorphanol, carfentanil, clonitazene, codeine, cyclorphen, cyprenorphine, desomorphine, dextromoramide, dezocine, diampromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, heroin, hydrocodone, hydroxymethylmorphinan, hydromorphone, hydroxypethidine, isomethadone, ketobemidone, levallorphan, levorphanol, levophenacylmorphan, lofentanil, meperidine, meptazinol, metazocine, methadone, methylmorphine, metopon, mirfentanil, morphine, morphine-6-glucuronide, myrophine, nalbuphine, narceine, nicomorphine, norlevorphanol, normethadone, nalorphine, nociceptinlorphanin FQ (N/OFQ), normorphine, norpipanone, ohmefentanyl, opium, oxycodone, oxymorphone, papaveretum, pentazocine, phenadoxone, phenomorphan, phenazocine, phenoperidine, pholcodine, piminodine, piritramide, propheptazine, promedol, profadol, properidine, propiram, propoxyphene, remifentanil, sufentanil, tapentadol, tramadol, trefentanil, tilidine, nalbuphine, or any opioid having agonist activity at an opioid receptor belonging to the phenanthrene, morphinan, benzomorphan, methadone, phenylpiperidine, propionanilide 4-anilidopiperidine, 4-aryl piperidines, and 4-Heteroarylpiperidines class, any opioid having agonist activity at an opioid receptor having the same pentacyclic nucleus as nalmefene, naltrexone, buprenorphine, levorphanol, meptazinol, pentazocine and dezocine, any drug having agonist activity at an opioid receptor which is a fentanyl analog, and prodrugs, analogs, derivatives, pharmaceutically acceptable salts thereof and mixtures thereof in racemic or enantiomeric form.

The ketorolac formulations described herein can also include an additional NSAID, e.g., salicylates, indomethacin, flurbiprofen, diclofenac, naproxen, piroxicam, tebufelone, ibuprofen, etodolac, nabumetone, tenidap, alcofenac, antipyrine, aminopyrine, dipyrone, aminopyrone, phenylbutazone, clofezone, oxyphenbutazone, prenazone, apazone, benzydamine, bucolome, cinchophen, clonixin, ditrazol, epirizole, fenoprofen, floctafenin, flufenamic acid, glaphenine, indoprofen, ketoprofen, loxoprofen, meclofenamic acid, mefenamic acid, niflumic acid, phenacetin, salidifamides, sulindac, suprofen, tolmetin, pharmaceutically acceptable salts thereof, and mixtures thereof.

Non-opioid and non-nsaid analgesics can also be combined with ketorolac. Such agents include without limitation acetaminophen and flupiritine.

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

1. Materials and Methods

The materials listed in Table 1 were purchased from the indicated supplier.

TABLE 1

Description of Materials Used

| Material | Supplier |
|---|---|
| Ketorolac tromethamine USP | Aldrich |
| H$_2$O (HPLC grade) | Fisher |
| D-(+)-trehalose dihydrate | Sigma |
| Ammonium acetate | Fluka |
| Dextrose monohydrate | Aldrich |
| Sodium phosphate dibasic | Aldrich |
| Citric acid | Aldrich |
| Ethanol | Aldrich |
| Phosphoric acid | EMD |
| Sodium chloride | Sigma |
| 1.0N HCl | BDH |
| 1.0N NaOH | Mallinckrodt |
| VWR 0.2 μm syringe filters | VWR |
| Baxter IntraVia Bags | VWR |

The development, manufacture, and analysis of all formulations was performed using the equipment listed in Table 2.

TABLE 2

Description of Equipment Used to Manufacture and Analyze Formulations

| Description | Model Number |
|---|---|
| VWR Stability Oven | 1370FM |
| VWR Stability Oven | 1370FM |
| VWR Stability Chamber | 9005L |
| Agilent HPLC | 1200 |
| Agilent HPLC | 1260 |
| Barnstead Autoclave | AS12 |
| Thermo Scientific pH Meter | Orion 3 Star |

*Autoclave located at Validation Resources, Bend, OR

The utilized HPLC method for purity analysis method is provided in Table 3:

TABLE 3

HPLC Parameters and Integration Events for the Purity Method

HPLC Run Parameters

| Column | Agilent Eclipse XDB-C18 4.6 × 150 mm (S/N: USKH048453) |
|---|---|
| Mobile Phase | 55:44:1 MeOH:H$_2$O:AcOH |
| Run time | 15 minutes |
| Retention time | Approximately 5.6 min |
| Flow rate | 1.2 mL/min |
| Injection volume | 10 μL |
| Observation wavelength | 254 nm, bandwidth = 16 |
| Column temperature | 27° C. |

Integration Events

| Skim valley ratio | 20.0 |
|---|---|
| Slope sensitivity | 0.7 |
| Peak width | 0.02 |
| Area reject | 1.0 |
| Height reject | 0.1 |
| Integration cutoff | <1.4 min |

Generation of Degradation Products:

Degradation products for ketorolac tromethamine were generated under acidic and basic conditions for reference when evaluating HPLC chromatograms for purity. This ensures differentiation between degradants, impurities, and peaks which are both impurities and degradants. For the acid-catalyzed degradation, 4.92 mg of ketorolac tromethamine was added to a scintillation vial, followed by 10 mL of H$_2$O, and the pH of the resulting colorless solution was adjusted to pH 1.60 with H$_3$PO$_4$. Aliquots of this solution were placed in capped amber HPLC vials in an 85° C. oven for the indicated amount of time, then analyzed by HPLC using the purity method outlined in Table 3. For the base catalyzed degradation, 4.92 mg of ketorolac tromethamine was added to a scintillation vial, followed by 10 mL of H$_2$O, and the resulting colorless solution was adjusted to pH 12.09 with NaOH. Aliquots of this solution were placed in capped amber HPLC vials in an 85° C. oven for the indicated amount of time, then analyzed by HPLC using the purity method outlined in Table 3. Table 6 summarizes the measured purity of ketorolac tromethamine after the indicated time.

Light Stability Study:

Ketorolac tromethamine (4.97 mg) was added to a scintillation vial, then 10 mL of H$_2$O was added volumetrically to produce a colorless solution. The clear scintillation vial was capped and placed on the windowsill, exposing the solution to both ambient light and temperature conditions. Aliquots (500 μL) were removed at various time points and diluted with an equal volume of H$_2$O in an amber HPLC vial. The diluted solution was then analyzed by HPLC for the purity of ketorolac tromethamine. Results are summarized in Table 11.

Stability Study A in HPLC Vials:

Stability study A was completed in amber HPLC vials to eliminate the potential incompatibility of a formulation with the RTU bag material. All formulations were prepared in 25 mL class A volumetric flasks. Table 4 lists the amounts of the given components in each formulation.

TABLE 4

Compositions of Formulations 1-12

| | Formulation | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Ketorolac tromethamine (mg) | 12.63 | 12.69 | 12.64 | 12.65 | 12.39 | 12.39 | 12.66 | 12.39 | 12.58 | 12.71 | 12.47 | 12.71 |
| Sodium chloride (mg) | 219.86 | 219.30 | 219.79 | 219.12 | 219.11 | 219.55 | 219.12 | 219.17 | 219.01 | 219.15 | 219.54 | 219.73 |
| Ammonium acetate (mg) | | | 19.28 | 19.28 | | | | 19.28 | | | 19.28 | |
| Citric acid (mg) | | | | | 68.34 | 68.48 | | | 68.79 | | | 68.39 |
| Sodium phosphate dibasic (mg) | | | | | 617.54 | 617.84 | | | 617.62 | | | 617.40 |
| Hydrochloric acid | pH ↓ | pH ↓ | pH ↓ | pH ↓ | | | pH ↓ | pH ↓ | | pH ↓ | pH ↓ | |
| Sodium hydroxide | pH ↑ | pH ↑ | pH ↑ | pH ↑ | | | pH ↑ | pH ↑ | | pH ↑ | pH ↑ | |
| Water | qs to 25 mL | qs to 25 mL | qs to 25 mL | qs to 25 mL | qs to 25 mL | qs to 25 mL | qs to 25 mL | qs to 25 mL | qs to 25 mL | qs to 25 mL | qs to 25 mL | qs to 25 mL |
| Ethanol (μL) | | 250 | | 250 | | 250 | | | | | | |
| Trehalose (mg) | | | | | | | 250.19 | 250.01 | 249.66 | | | |
| Dextrose (mg) | | | | | | | | | | 250.15 | 250.47 | 250.69 |
| Ketorolac concentration (μg/mL) | 505.2 | 507.6 | 505.6 | 506.0 | 495.6 | 495.6 | 506.4 | 495.6 | 503.2 | 508.4 | 498.8 | 508.4 |
| Osmolarity (mOsmol/L) | 303.7 | 474.2 | 323.6 | 493.9 | 727.4 | 899.4 | 329.1 | 349.1 | 753.8 | 358.2 | 378.8 | 783.8 |
| Final pH | 7.50 | 7.38 | 6.89 | 7.04 | 7.04 | 7.05 | 7.51 | 7.04 | 7.02 | 7.40 | 7.00 | 7.05 |

Once all the components had been added to the flask, the flask was filled to the line with H₂O and mixed using a magnetic stir bar until completely in solution. The pH of the formulation was adjusted to the value given in Table 4 using 1.0N NaOH or 1.0N HCl. Each formulation was purged with N₂ for 5 minutes, then the solution was filtered through a 0.2 μm syringe filter before 1.6 mL aliquots were transferred into 14 separate amber HPLC vials. Seven vials were then capped, while the headspace of the remaining 7 vials was purged with N₂ and capped immediately. Twelve vials were then placed in a 121° C. oven for 20 minutes to simulate autoclave conditions. Following the simulated autoclave conditions, the samples were transferred into the 40° C./75% RH stability chamber to initiate the stability study. At times of 0, 1, 4, 7, 10 and 14 days, the sample was removed from the stability chamber and analyzed by HPLC for the purity of ketorolac tromethamine within 24 hours. The purity results for all formulations are list in Table 7.

Stability Study B in Baxter IntraVia Bags:

Stability formulations were prepared in 2 L class A volumetric flasks, using the materials listed in Table 5:

TABLE 5

Composition of Formulations 7, 8, and 10 for RTU Bag Stability Study

| | Formulation #7 | Formulation #8 | Formulation #10 |
|---|---|---|---|
| Ketorolac tromethamine | 1.00047 g | 1.00048 g | 1.00093 g |
| Sodium chloride | 17.542 g | 17.536 g | 17.532 g |
| Trehalose | 20.015 g | 20.011 g | — |
| Dextrose | — | — | 20.008 g |
| Ammonium acetate | — | 1.544 g | — |
| Water | qs to 2 L | qs to 2 L | qs to 2 L |
| pH | 7.45 | 6.94 | 7.38 |
| Osmolarity (mOsmol/L) | 329.3 | 329.2 | 358.2 |
| Ketorolac concentration (μg/mL) | 500.2 | 500.2 | 500.5 |

Once all materials were added to the volumetric flask, it was filled to the line with H₂O. The flask was magnetically stirred if any undissolved material was present. If necessary, the pH of the formulation was adjusted using 1.0N NaOH or 1.0N HCl to the final value given in Table 5. The formulations were then purged with N₂ for 5 minutes before the bag filling process began. The Baxter IntraVia bags were filled by mass (80g±1 g) using a peristaltic pump to feed the solution into each bag. A 2-way valve were placed in the solution filling line for sterile filtration and to regulate flow, respectively. For each formulation, 24 bags were filled.

All bags were used in the stability study without exposure to autoclave (or simulated autoclave) conditions. All bags were pulled within 1 day time points of 0, 4, 7, 14, 28 and 42 days and allowed to equilibrate to room temperature before sampling. Sampling of the bags for HPLC analysis occurred using a 5cc disposable syringe with 21 gauge needle through the drug injection port. Approximately 1.5 mL of each formulation was transferred to an amber HPLC vial and analyzed within 12 hours of sampling. Results from the purity analysis are summarized in Table 8.

Determination of Osmolarity:

The osmolarity of the individual formulations were determined as per USP <785> guidelines, using equation (1):

$$\text{Osmolarity (mOsmol/L)} = \left(\frac{\text{wt. of substance (g/L)}}{\text{mol wt. (g)}}\right) \times (\text{number of species}) \times (1000) \quad (1)$$

The osmolarity of each individual component in the formulation is calculated and the sum of these values (the total osmolarity) is the value provided in tables 4 and 5 for the glass and bag stability studies, respectively.

Stability Predictions using the Arrhenius Equation:

Long-term stability predictions were completed using Agere's stability prediction algorithms, based on the Arrhenius equation (2):

$$k = Ae^{\frac{-E_a}{RT}} \quad (2)$$

Where k is the rate constant, A is the pre-exponential factor, $E_a$ is the activation energy, T is the temperature (in degrees Kelvin), and R is the gas constant (taken to be 8.31446 $J \cdot mol^{-1} \cdot K^{-1}$). The acquired HPLC purity data is plotted and fit to a trend line, then the Arrhenius equation parameters are extrapolated to determine the rate constant at a given temperature. This rate constant represents the rate of degradation of ketorolac tromethamine. Using this rate constant, the long-term stability of a formulation can be predicted. The values of the extrapolated Arrhenius parameters are supplied in Table 10.

2. Results and Discussion

Acid- and base-catalyzed degradation experiments were performed. After 40 hours, both conditions provided significant degradation, affording chromatograms with identifiable degradation peaks. As reported in Gu, L. et al. (International Journal of Pharmaceutics. (1988), 41, 95-104) there are two primary degradation pathways for ketorolac tromethamine (Scheme 1):

Scheme 1: Primary Degradation Mechanisms for Ketorolac Tromethamine

Table 6 summarizes the purity of ketorolac tromethamine measured by HPLC in the acid- and base-catalyzed degradation experiments. The number of degradation peaks observed in the base-catalyzed experiment is higher, although the magnitude (and integral of) the degradation peaks in the acid-catalyzed experiment is greater, yielding a lower purity.

TABLE 6

HPLC Purity of Ketorolac Tromethamine Under Acid- and Base-catalyzed Degradation Conditions

| Condition | 1.5 hours | 2.5 hours | 4 hours | 24 hours | 40 hours |
|---|---|---|---|---|---|
| Acid | 99.02% | 98.96% | 98.92% | 98.87% | 98.08% |
| Base | 99.67% | 99.66% | 99.62% | 99.28% | 98.97% |

HPLC purity of formulations in amber HPLC vials is provided in Table 7. $N_2$ headspace has little effect on all formulations and was not included as a parameter.

TABLE 7

HPLC Purity of Stage II Formulations

| Formulation | $N_2$ Headspace | Pre-autoclave | 0 days | 1.5 days | 4 days | 6.5 days | 10.5 days | 14 days |
|---|---|---|---|---|---|---|---|---|
| 1 | + | 99.75 | 99.75 | 99.75 | 99.75 | 99.75 | 99.75 | 99.74 |
|   | − | 99.75 | 99.75 | 99.75 | 99.75 | 99.75 | 99.75 | 99.75 |
| 2 | + | 99.74 | 99.73 | 99.74 | 99.74 | 99.74 | 99.73 | 99.74 |
|   | − | 99.73 | 99.73 | 99.74 | 99.74 | 99.74 | 99.73 | 99.73 |
| 3 | + | 99.75 | 99.75 | 99.75 | 99.75 | 99.76 | 99.75 | 99.75 |
|   | − | 99.75 | 99.75 | 99.75 | 99.76 | 99.76 | 99.75 | 99.75 |
| 4 | + | 99.74 | 99.75 | 99.75 | 99.75 | 99.75 | 99.75 | 99.75 |
|   | − | 99.75 | 99.74 | 99.74 | 99.75 | 99.75 | 99.74 | 99.75 |
| 5 | + | 99.75 | 99.75 | 99.71 | 99.70 | 99.70 | 99.67 | 99.67 |
|   | − | 99.76 | 99.75 | 99.73 | 99.71 | 99.70 | 99.67 | 99.67 |
| 6 | + | 99.75 | 99.75 | 99.75 | 99.75 | 99.76 | 99.75 | 99.75 |
|   | − | 99.76 | 99.75 | 99.75 | 99.76 | 99.75 | 99.75 | 99.75 |
| 7 | + | 99.74 | 99.74 | 99.74 | 99.74 | 99.75 | 99.74 | 99.75 |
|   | − | 99.74 | 99.74 | 99.74 | 99.75 | 99.75 | 99.74 | 99.74 |
| 8 | + | 99.74 | 99.75 | 99.75 | 99.75 | 99.76 | 99.74 | 99.75 |
|   | − | 99.74 | 99.74 | 99.75 | 99.76 | 99.75 | 99.75 | 99.75 |

TABLE 7-continued

HPLC Purity of Stage II Formulations

| Formulation | N₂ Headspace | Pre-autoclave | 0 days | 1.5 days | 4 days | 6.5 days | 10.5 days | 14 days |
|---|---|---|---|---|---|---|---|---|
| 9 | + | 99.74 | 99.74 | 99.72 | 99.71 | 99.70 | 99.67 | 99.67 |
|   | − | 99.76 | 99.75 | 99.72 | 99.71 | 99.70 | 99.67 | 99.69 |
| 10 | + | 99.74 | 99.74 | 99.75 | 99.75 | 99.75 | 99.75 | 99.75 |
|   | − | 99.75 | 99.75 | 99.75 | 99.75 | 99.75 | 99.75 | 99.75 |
| 11 | + | 99.73 | 99.73 | 99.73 | 99.73 | 99.73 | 99.73 | 99.73 |
|   | − | 99.73 | 99.73 | 99.73 | 99.73 | 99.73 | 99.73 | 99.73 |
| 12 | + | 99.76 | 99.54 | 99.42 | 99.38 | 99.20 | 98.57 | 98.56 |
|   | − | 99.76 | 99.46 | 99.58 | 99.53 | 99.44 | 98.94 | 98.40 |

This study included 3 formulations at 3 different temperatures (40° C., 60° C., and 80° C.) with time points over 6 weeks. Stability Study A provided information to structure Stability Study B with respect to the ideal parameters. The primary difference between the two studies is the need to sample from the Baxter IntraVia bags, which showed degradation. The two-port IntraVia bags were stable and showed no degradation at 40° C., while at 60° C. and 80° C. the bags began to melt to the aluminum foil on which they were placed over time. The ports began to become brown and a salty residue was observed on the outside of the port upon sampling. Table 8 details the measured purity by HPLC of formulations 7, 8, and 10.

TABLE 8

HPLC Purity of Formulations 7, 8, and 10 in Baxter IntraVia Bags

| Formulation | Temp (° C.) | t = 0 | 1 day | 2 days | 4 days | 7 days | 14 days | 28 days | 42 days |
|---|---|---|---|---|---|---|---|---|---|
| 7 | 40 | 99.77 |  |  | 99.76 | 99.76 | 99.75 | 99.74 | 99.75 |
|   | 60 | 99.77 |  | 99.76 | 99.77 | 99.75 | 99.77 | 99.68 |  |
|   | 80 | 99.77 | 99.76 | 99.76 | 99.70 | 99.71 | 99.59 | 98.67 |  |
| 8 | 40 | 99.78 |  |  | 99.75 | 99.76 | 99.75 | 99.74 | 99.74 |
|   | 60 | 99.78 |  | 99.76 | 99.76 | 99.75 | 99.72 | 99.69 |  |
|   | 80 | 99.78 | 99.75 | 99.75 | 99.71 | 99.68 | 99.50 | 98.85 |  |
| 10 | 40 | 99.77 |  |  | 99.76 | 99.76 | 99.75 | 99.76 | 99.75 |
|   | 60 | 99.77 |  | 99.76 | 99.77 | 99.76 | 99.71 | 99.67 |  |
|   | 80 | 99.77 | 99.77 | 99.76 | 99.73 | 99.59 | 98.61 | 97.19 |  |

As experienced in the Stability Study A, all formulations exhibited minimal degradation at 40° C., while at 60° C. the formulations show only slight degradation. Only at 80° C. do all formulations start to degrade at a higher rate. This observation is supported by the relatively high activation energies extrapolated from the Arrhenius equation (provided in Table 10). The degradation of ketorolac tromethamine observed in this study requires substantial amounts of energy, only achievable with high temperatures. The one and two year purity projections are given in Table 9 and plotted in FIG. 1.

TABLE 9

Projected Purity of Formulations in Baxter IntraVia Bags at 25° C.

| Formulation | Initial purity | Projected (1 year) | Projected (2 years) |
|---|---|---|---|
| 7 | 99.77 | 99.72 | 99.66 |
| 8 | 99.78 | 99.68 | 99.59 |
| 10 | 99.77 | 99.75 | 99.73 |

Alternative degradation mechanisms exist for ketorolac tromethamine which do not necessitate high temperature but rather exposure to ambient light sources. The ambient light stability study affords results are set forth in Table 11.

TABLE 10

Extrapolated Values of Arrhenius Equation Parameters

| Formulation | $E_a$ (kJ/mol) | ln(A) | k at 25° C. | $R^2$ for ln(A) vs. 1/T plot |
|---|---|---|---|---|
| 7 | 81.54 | 24.08 | 1.483E−04 | 0.933 |
| 8 | 71.34 | 20.51 | 2.557E−04 | 0.918 |
| 10 | 113.00 | 35.75 | 5.379E−05 | 0.964 |

TABLE 11

HPLC Purity of Ambient Light Stability Samples

| Pull Time (days) | Purity |
|---|---|
| 0 | 99.62% |
| 1 | 99.62% |
| 3 | 99.60% |
| 5 | 99.61% |
| 12 | 99.60% |
| 41 | 97.03% |
| 48 | 96.24% |
| 62 | 93.27% |
| 76 | 90.50% |

Following the 42 day stability pull of formulations 7, 8, and 10 in Baxter IntraVia bags, the pH of the formulations were measured for comparison to the initial value. The results of these measurements are tabulated in Table 12.

TABLE 12 pH change of Formulations in Baxter IntraVia Bags

| | Formulation 7 | Formulation 8 | Formulation 10 |
|---|---|---|---|
| Initial pH (t = 0) | 7.5 | 6.9 | 7.4 |
| 40° C. (t = 42 days) | 7.1 | 7.5 | 4.6 |
| 60° C. (t = 42 days) | 6.9 | 6.1 | 5.7 |

A number of factors can have a significant effect on the measured pH of the solution. Primarily, extended exposure to high temperatures can concentrate the samples contained in the bag by evaporation through the semi-permeable bag material, as evidenced by the measured concentrations of the longer-term, high temperature stability samples. Alternatively, carbon dioxide can be absorbed through the bag material, which is then converted to carbonic acid in solution. In formulation 8 (containing ammonium acetate), ammonia gas can be absorbed into the bag material, leaving the acetate anion which becomes protonated in solution to form acetic acid. All of these situations can alter the pH of a formulation, however, all of these measured pH's are within range of those acceptable for injectable solutions.

Determination of Dissolved Oxygen:

Procedure:
1. Samples were transferred to 100 mL BOD bottles and measured with oxygen meter for dissolved oxygen (Test 1).
2. Samples were autoclaved for 15 minutes at 121° C., removed from autoclave, bottles were immediately capped, and cooled to room temperature in a water bath, at 24° C. and then measured with oxygen meter for dissolved oxygen (Tests 2, 3 and 4).

TABLE 13

Dissolved Oxygen

| Formulation | Dissolved Oxygen mg/L Test 1 | Dissolved Oxygen mg/L Test 2 | Dissolved Oxygen mg/L Test 3 | Dissolved Oxygen mg/L Test 4 |
|---|---|---|---|---|
| 7 | 9.71 | 9.68 | 9.29 | 9.96 |
| 8 | 9.76 | 8.32 | 9.07 | 9.41 |
| 10 | 9.53 | 8.84 | 9.48 | 8.98 |

3. Conclusion

Ketorolac tromethamine is shown to be stable upon exposure to heat for extended periods of time. This observation is supported by the extrapolated parameters from the Arrhenius equation, and specifically, the activation energy. The primary risk for a ketorolac-containing formulation is light instability which can be mitigated by use of a foil over pouch to protect from ambient light sources. A predicted stable for a minimum of 2 years is predicted based on, e.g., a formulation as disclosed herein in Baxter IntraVia bags with the addition of a foil over pouch.

We claim:

1. A method of providing analgesia to a patient in need thereof comprising administering a bolus dose of ketorolac to achieve a rapid analgesic response, followed by continuous infusion of a composition to maintain analgesic response, the composition comprising:
   an aqueous solution comprising ketorolac or a pharmaceutically acceptable salt thereof in an amount from about 0.1 mg/mL to about 10 mg/mL; and
   a pharmaceutically acceptable excipient selected from a group consisting of trehalose, anhydrous or hydrous forms of sodium chloride, dextrose, sucrose, xylitol, fructose, glycerol, sorbitol, mannitol, potassium chloride, mannose, calcium chloride and magnesium chloride;
   wherein the composition is free of alcohol,
   wherein the composition maintains at least 90% of the amount of ketorolac or a pharmaceutically acceptable salt thereof after storage for 6 months at 25° C.

2. A method of treating analgesia comprising parenterally administering a composition by continuous infusion to a patient in need thereof, the composition comprising:
   an aqueous solution comprising ketorolac or a pharmaceutically acceptable salt thereof in an amount from about 0.1 mg/mL to about 10 mg/mL; and
   a pharmaceutically acceptable excipient selected from a group consisting of trehalose, anhydrous or hydrous forms of sodium chloride, dextrose, sucrose, xylitol, fructose, glycerol, sorbitol, mannitol, potassium chloride, mannose, calcium chloride and magnesium chloride;
   wherein the composition is free of alcohol,
   wherein the composition maintains at least 90% of the amount of ketorolac or a pharmaceutically acceptable salt thereof after storage for 6 months at 25° C.

3. The method of claim 2, wherein the continuous infusion is from about 0.5 mg to about 5 mg per hour, from about 1 mg to about 4 mg per hour, or from about 2 mg to about 3 mg per hour.

4. The method of claim 1, wherein the bolus dosing is from about 10 mg to about 50 mg, from about 20 mg to about 40 mg, or about 30 mg.

5. The method of claim 1, wherein the excipient comprises trehalose.

6. The method of claim 1, wherein the composition maintains at least 90% of the amount of ketorolac or a pharmaceutically acceptable salt thereof after storage for 1 year at 25° C.

7. The method of claim 1, wherein the composition has a pH from about 4.5 to about 8.5.

8. The method of claim 1, wherein the pharmaceutically acceptable salt is ketorolac tromethamine.

9. The method of claim 1, wherein the osmolality of the composition is in the range from about 250 to 350 mOsm/kg.

10. The method of claim 1, wherein the composition is free of a sugar alcohol.

11. The method of claim 1, wherein the composition has an activation energy (Ea) of at least 60 kJ/mol.

12. The method of claim 1, wherein the composition has a dissolved oxygen content of less than 15 mg/L.

13. The method of claim 2, wherein the excipient comprises trehalose.

14. The method of claim 2, wherein the composition maintains at least 90% of the amount of ketorolac or a pharmaceutically acceptable salt thereof after storage for 1 year at 25° C.

15. The method of claim 2, wherein the composition has a pH from about 4.5 to about 8.5.

16. The method of claim 2, wherein the pharmaceutically acceptable salt is ketorolac tromethamine.

17. The method of claim 2, wherein the osmolality of the composition is in the range from about 250 to 350 mOsm/kg.

18. The method of claim 2, wherein the composition is free of a sugar alcohol.

19. The method of claim 2, wherein the composition has an activation energy (Ea) of at least 60 kJ/mol.

20. The method of claim 2, wherein the composition has a dissolved oxygen content of less than 15 mg/L.

21. A method of providing analgesia to a patient in need thereof comprising administering a bolus dose of ketorolac to achieve a rapid analgesic response, followed by continuous infusion of a composition to maintain analgesic response, the composition comprising:
- an aqueous solution comprising ketorolac or a pharmaceutically acceptable salt thereof; and
- a pharmaceutically acceptable excipient selected from a group consisting of trehalose, anhydrous or hydrous forms of sodium chloride, dextrose, sucrose, xylitol, fructose, glycerol, sorbitol, mannitol, potassium chloride, mannose, calcium chloride and magnesium chloride;
- wherein the composition is free of alcohol and maintains at least 90% of the amount of ketorolac or a pharmaceutically acceptable salt thereof after storage for 6months at 25° C.

* * * * *